United States Patent [19]

Kardorff et al.

[11] Patent Number: 5,132,326
[45] Date of Patent: Jul. 21, 1992

[54] CYCLOPROPANETHIOCARBOXAMIDES

[75] Inventors: Uwe Kardorff, Mannheim; Joachim Leyendecker, Ladenburg; Hans-Juergen Neubauer, Muenster; Christoph Kuenast, Otterstadt; Peter Hofmeister, Neustadt; Wolfgang Krieg, Weingarten, all of Fed. Rep. of Germany

[73] Assignee: BASF Aktiengesellschaft, Ludwigshafen, Fed. Rep. of Germany

[21] Appl. No.: 561,613

[22] Filed: Aug. 2, 1990

[30] Foreign Application Priority Data

Aug. 10, 1989 [DE] Fed. Rep. of Germany ....... 3926468

[51] Int. Cl.$^5$ ............................................. A01N 37/18
[52] U.S. Cl. .................................... 514/599; 514/524; 558/412; 564/74
[58] Field of Search ................... 564/74; 514/599, 524; 558/412

[56] References Cited

U.S. PATENT DOCUMENTS 4,625,048 11/1986 Zurflüh .................................. 564/74
4,859,706 8/1989 Buerstinghaus et al. ............ 514/624

FOREIGN PATENT DOCUMENTS 0350688 7/1988 European Pat. Off. .
52-128220 4/1976 Japan .

Primary Examiner—Richard L. Raymond
Assistant Examiner—Scott C. Rand
Attorney, Agent, or Firm—Keil & Weinkauf

[57] ABSTRACT

Cyclopropanethiocarboxamides I

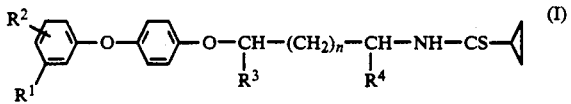

($R^1$, $R^2$=H, CN, $NO_2$, halogen, $C_1$-$C_4$-alkyl, $C_1$-$C_4$-alkoxy, $C_1$-$C_4$-haloalkyl, $C_1$-$C_4$-haloalkoxy; $R^3$, $R^4$=H, $C_1$-$C_4$-alkyl; n=0 or 1).

The compounds I are suitable as pesticides.

11 Claims, No Drawings

CYCLOPROPANETHIOCARBOXAMIDES

The present invention relates to novel cyclopropanethiocarboxamides of the general formula I

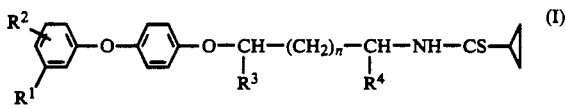

where
$R^1$ and $R^2$ are each hydrogen, cyano, nitro, halogen, $C_1$–$C_4$-alkyl or $C_1$–$C_4$-alkoxy, and the alkyl and alkoxy radicals may be partially or completely halogenated, $R^3$ and $R^3$ are each hydrogen or $C_1$–$C_4$-alkyl and n is 0 or 1.

The present invention further more relates to a process for the preparation of these compounds, their use for pest control and agents which contain these compounds as active substances.

DE-A 36 28 082 discloses N-[2-(4- phenoxyphenoxy)ethyl]-cyclopropanecarboxamides as pesticidal compounds.

However, the action of these known pesticides on the pests and the duration of their action is satisfactory only to a limited extent.

It is an object of the present invention to provide novel pesticides with which the pests can be controlled better than in the past.

We have found that this object is achieved by the cyclopropanethiocarboxamides of the general formula I which were defined at the outset.

The substituents in the novel compounds I have the following specific meanings:

$R^1$ is hydrogen, cyano or nitro;
halogen, including preferably fluorine, chlorine or bromine;
straight chain or branched $C_1$–$C_4$-alkyl, such as methyl, ethyl, propyl, isopropyl, butyl, isobutyl, sec-butyl or tert-butyl, preferably methyl, ethyl, isopropyl, isobutyl or sec-butyl; straight-chain or branched $C_1$–$C_4$-alkoxy, preferably methoxy, ethoxy or isopropoxy;

partially or completely halogenated $C_1$–$C_4$-alkyl, preferably straight-chain or branched $C_1$–$C_4$-fluoro- or $C_1$–$C_4$-chloroalkyl, such as fluoromethyl, difluoromethyl, trifluoromethyl, 2,2,2-trifluoroethyl, pentafluoroethyl, trichloromethyl or 2,2,2-trichloroethyl;

partially or completely halogenated $C_1$–$C_4$-alkoxy, preferably straight-chain or branched $C_1$–$C_4$-fluoro- or $C_1$–$C_4$-chloroalkoxy, such as trifluoromethoxy, 1,1,2,2-tetrafluoroethoxy, pentafluoroethoxy or trichloromethoxy;

$R^2$ is preferably in the 4-position of the phenyl ring and has the same meanings as $R^1$; and $R^3$ and $R^4$ are each hydrogen, methyl, ethyl, propyl, isopropyl, butyl, isobutyl, sec-butyl or tert-butyl, preferably methyl or ethyl.

Particularly suitable compounds I are those in which $R^3$ and $R^4$ are each hydrogen and n is 0. Preferred compounds I are described in the Examples.

The novel compounds I can be prepared by conventional methods of thiocarboxamide synthesis (cf. C. Ferri, Reaktionen der organischen Synthese, Georg Thieme Verlag, Stuttgart 1978, page 549 et seq.), for example by sulfurization of the corresponding cyclopropanecarboxamides with $P_4S_{10}$ or with Lawesson reagent (2,4-bis-(4-methoxyphenyl)-2,4-dithioxo-1,3,2,4-dithiadiphosphetane).

The compounds I are particularly advantageously obtained by reacting a 4-phenoxyphenoxyalkylamine II

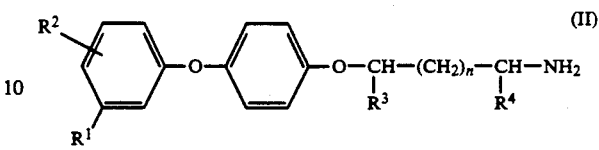

with a cyclopropanedithiocarboxylate III

preferably a $C_1$–$C_6$-alkyl ester, especially the methyl ester.

The starting compounds II and III are preferably used in a stoichiometric ratio, but in some cases an excess of one or other component, for example not more than 10%, may be preferable.

The reaction usually takes place at an adequate rate at above $-30°$ C. In general, the temperature is from $-30°$ to $130°$C., in particular from $-10°$ to $80°$ C., preferably from $0°$ to $50°$ C.

It is advantageously carried out in a solvent or diluent at atmospheric pressure. A lower or higher pressure is possible but generally has no advantages.

Suitable solvents or diluents are aliphatic and aromatic hydrocarbons and chlorohydrocarbons, such as petroleum ether, n-pentane, n-hexane, hexane isomer mixtures, benzene, toluene, xylene, gasoline, dichloromethane, chloroform, carbon tetrachloride, 1,2-dichloroethane and chlorobenzene, ethers, such as diethyl ether, di-n-butyl ether, methyl tert-butyl ether, tetrahydrofuran and dioxane, esters, such as ethyl acetate, ketones, such as acetone, methyl ethyl ketone and methyl isopropyl ketone, nitriles, such as acetonitrile and propionitrile, alcohols, such as methanol, ethanol, n-propanol and isopropanol, and aprotic dipolar solvents, such as dimethylformamide, dimethyl sulfoxide and pyridine. Mixtures of these substances can also be used as solvents and diluents.

Some of the 4-phenoxyphenoxyalkylamines II required for preparation of the compound I are known from Houben/Weyl, Vol. VI/3, Methoden der organischen Chemie, Thieme Verlag, 1965, page 85 et seq.; those which are unknown can be prepared by the methods described there.

The cyclopropanedithiocarboxylates III additionally required are known from C. R. Acad. Sci., Ser. C, 274, (1972), 642 or can be prepared by the method described there. They are obtained, for example, by subjecting the cyclopropyl bromide, magnesium and carbon disulfide to a Grignard reaction and then reacting the resulting Grignard compound with an alkyl iodide, preferably methyl iodide.

Some of the novel compounds I are obtained in the form of colorless or slightly brownish oils, which can be freed from the final volatile constituents by prolonged heating to moderately elevated temperatures under reduced pressure (incipient distillation) and can be purified in this manner. If the compounds of the formula I are obtained in crystalline form, they can be purified by recrystallization.

The novel compounds I may contain one or more centers of asymmetry. They are obtained as racemates in most preparation processes but can, if desired, also be separated into the pure isomers by conventional methods, for example by chromatography over an optically active adsorbent.

In contrast to most of the pesticides known to date, which are contact or ingested poisons and thus kill, incapacitate or repel the animals, the compounds of the formula I intervene in the hormone system of the animal organism. In the case of insects, for example, the transformation to the imago, the laying or viable eggs and the development of normal laid eggs is disturbed and the sequence of generations is thus interrupted. The novel agents are virtually completely nontoxic to vertebrates.

Preparation Example

[N-[4-(3-Fluorophenoxy)-phenoxy]-ethyl]cyclopropanethiocarboxamide

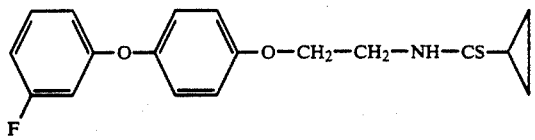

A solution of 2.4 g (9.7 mmol) or [4-(3-fluorophenoxy)-phenoxy]-ethylamine, 1.3 g (9.7 mmol) of methyl cyclopropanedithiocarboxylate and 40 ml of toluene were stirred for 14 hours at 20° C., after which the readily volatile substances were distilled off under reduced pressure. The residue was recrystallized from ethyl acetate/n-hexane. The product was obtained in the form of colorless crystals in a yield of 75%.

$^1$H-NMR spectrum (300 MHz, $d^6$-DMSO, tetramethysilane as standard [0 ppm]): 0.68–1.2 ppm (m, 4 H); 2.05–2.30 ppm (m, 1 H); 3.92 ppm (t, 2 H); 4.21 ppm (t, 2H); 6.58–7.42 ppm (m, 8 H); 10.38 ppm (s, 1 H).

Further physical data are shown in the Table below, which lists other compounds which were prepared, or can be prepared, in a similar manner.

TABLE 1

Novel cyclopropanethiocarboxamides

| No. | n | R$^1$ | R$^2$ | R$^3$ | R$^4$ | mp. [°C.] | IR data [cm$^{-1}$] | Yield [%] |
|---|---|---|---|---|---|---|---|---|
| 1 | O | F | H | H | H | 69 | 1507, 1487, 1248, 1240, 1209, 1121, 962, 848, 841 | 75 |
| 2 | O | H | H | H | H | 60–62 | 1504, 1488, 1247, 1235, 1194, 994, 832 | 73 |
| 3 | O | H | 4-F | H | H | 65 | 1504, 1250, 1231, 1192, 1064, 994, 827 | 50 |
| 4 | O | Cl | H | H | H | 101 | 1505, 1472, 1464, 1216, 1192, 1056, 995, 967, 842 | 62 |
| 5 | O | Br | H | H | H | 56–57 | 1505, 1489, 1468, 1229, 1222, 1058, 994 | 83 |
| 6 | O | Cl | 4-F | H | H | 99–100 | 1507, 1493, 1463, 1247, 1209, 1054, 998, 845, 784 | 68 |
| 7 | O | CH$_3$ | H | H | H | oil | 1502, 1486, 1464, 1328, 1256, 1240, 1208, 1059, 996 | 81 |
| 8 | O | CF$_3$ | H | H | H | oil | 1503, 1491, 1450, 1328, 1221, 1191, 1170, 1126, 1064, 914 | 90 |
| 9 | O | C$_2$H$_5$ | H | H | H | oil | 1502, 1485, 1465, 1447, 1328, 1233, 1207, 1059, 996 | 87 |
| 10 | O | OCH$_3$ | H | H | H | | | |
| 11 | O | Cl | 4-Cl | H | H | | | |
| 12 | O | OCF$_3$ | H | H | H | | | |
| 13 | O | H | 4-Cl | H | H | | | |
| 14 | O | H | 4-Br | H | H | | | |
| 15 | O | NO$_2$ | H | H | H | | | |
| 16 | O | F | H | CH$_3$ | H | | | |
| 17 | O | H | H | CH$_3$ | H | | | |
| 18 | O | H | 4-F | CH$_3$ | H | | | |
| 19 | O | Cl | H | CH$_3$ | H | | | |
| 20 | O | Br | H | CH$_3$ | H | | | |
| 21 | O | Cl | 4-F | CH$_3$ | H | | | |
| 22 | O | CH$_3$ | H | CH$_3$ | H | | | |
| 23 | O | CF$_3$ | H | CH$_3$ | H | | | |
| 24 | O | C$_2$H$_5$ | H | CH$_3$ | H | | | |
| 25 | O | OCH$_3$ | H | CH$_3$ | H | | | |
| 26 | O | Cl | 4-Cl | CH$_3$ | H | | | |
| 27 | O | OCF$_3$ | H | CH$_3$ | H | | | |
| 28 | O | H | 4-Cl | CH$_3$ | H | | | |
| 29 | O | H | 4-Br | CH$_3$ | H | | | |
| 30 | O | NO$_2$ | H | CH$_3$ | H | | | |
| 31 | O | F | H | H | CH$_3$ | | | |
| 32 | O | H | H | H | CH$_3$ | | | |
| 33 | O | H | 4-F | H | CH$_3$ | | | |
| 34 | O | Cl | H | H | CH$_3$ | | | |
| 35 | O | Br | H | H | CH$_3$ | | | |
| 36 | O | Cl | 4-F | H | CH$_3$ | | | |
| 37 | O | CH$_3$ | H | H | CH$_3$ | | | |

TABLE 1-continued

Novel cyclopropanethiocarboxamides

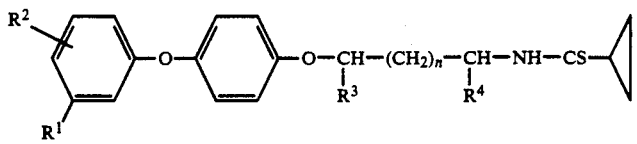

| No. | n | R¹ | R² | R³ | R⁴ | mp. [°C.] IR data [cm⁻¹] | Yield [%] |
|---|---|---|---|---|---|---|---|
| 38 | O | CF₃ | H | H | CH₃ | | |
| 39 | O | C₂H₅ | H | H | CH₃ | | |
| 40 | O | OCH₃ | H | H | CH₃ | | |
| 41 | O | Cl | 4-Cl | H | CH₃ | | |
| 42 | O | OCF₃ | H | H | CH₃ | | |
| 43 | O | H | 4-Cl | H | CH₃ | | |
| 44 | O | H | 4-Br | H | CH₃ | | |
| 45 | O | NO₂ | H | H | CH₃ | | |

The cyclopropanethiocarboxamides are suitable for effectively combating pests such as insects, arachnids and nematodes. They may be used as pesticides in crop protection and in the hygiene, stores protection and veterinary sector.

Examples of injurious insects belonging to the Lepidoptera order are *Argotis ypsilon, Argotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Cholistoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phtorimaea operculella, Phyllocnistis citrella, Pieris brassicae, Phathpena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Argiotes lineatus, Argiotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcatra, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorphoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Lirimyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integricipes, Euchistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhpalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*.

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae*.

Examples from the nematodes class are root-knot nematodes, e.g., *Meloidogyne hapla, Meloidogyne incognita* and *Meloidogyne javanica*, cyst-forming nematodes, e.g., *Globodera rostochiensis, Heterodera avenae, Hetrodera glycinae, Heterodera schachtii* and *Heterodera trifolii*, and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, napthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dust and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 3 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 4 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 5 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcuim sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90% by weight of active ingredient.

The active ingredient concentrations in the finished formulations may vary over a wide range. Generally, they are from 0.0001 to 10, and preferably from 0.01 to 1.0, %.

The active ingredients may also successfully be used in the ultra-low-volume (ULV) method, where it is possible to apply formulations containing more than 95wt% of active ingredient, or even the active ingredient without additives.

In the open, the amount of active ingredient applied is for example from 0.02 to 10, particularly from 0.1 to 2.0, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

Use examples

The concentrations at which the compounds investigated achieved 100% or 80% kill or inhibition are the minimum concentrations in each case (action threshold).

The purity of the active ingredients was >95%.
The following formulations were used:

(a) a 0.1% solution of the active ingredient in acetone, which was further diluted with acetone according to the stated dosage rates;

(b) a 10% emulsion of the active ingredient in a mixture consisting of 70wt% of cyclohexanone, 20wt% of Nekanil ®LN (ΔLutensol AP6, a spreadsticker with an emulsifying and dispersing action based on ethoxylated alkylphenols) and 10wt% of Emulphor ®EL (ΔEmulan-®EL, an emulsifier based on ethoxylated fatty alcohols). The concentrations given in the examples were obtained by diluting the formulated active ingredient with water.

EXAMPLE A

Ovicidal action on *Dysdercus intermedius* (cotton stainer)

Pieces of double sided adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent to eggs coming into contact with the paper.

The markers were then placed in plastic trays (adhesive strip at the top). Half a roll of absorbent cotton was moistened with water and placed in each beaker to prevent drying out, and the trays were covered with a glass plate. Assessment took place after 8 days (control bugs hatched).

At an active ingredient concentration of 0.1 to 10 ppm, compounds 1, 3, 4, 5, 6 and 7 achieved 80 to 100% kill.

EXAMPLE B

*Dysdercus intermedius* (cotton stainer); breeding experiment

The experiment was carried out in 1 liter jars containing 200 g of sterile quartz sand to which 25 ml of aqueous active ingredient formulations had been admixed. Approx. 20 larvae of the third stage were then introduced into each jar. The food proffered was swollen cottonseed, which was changed once a week. The sand was also moistened once a week. The experiment was run until the subsequent generation hatched. The action in percentage kill was then assessed.

At an active ingredient concentration of 0.1 to 1 ppm, compounds 1 to 7 and 9 achieved 100% kill.

EXAMPLE C

Breeding experiment with *Musca domestica* (housefly)

The experiment was run in 100 ml plastic beakers. 25 ml of a dry feed mix (1 g of bran, 250 g of yeast powder and 35 g of fishmeal) was introduced into the beakers, the active ingredients were added together with 25 ml of a solution of milk and sugar (1 liter of milk and 42 cm$^3$ of sugar). 20 larvae in the first larval stage were then placed in each beaker. Perforated lids were then placed on the beakers. The experiment was run until the flies in a control experiment (without active ingredient) hatched.

At a concentration of 20 to 40 ppm, compounds 1, 3, 4, 5, 6, 7 and 9 achieved 100% kill.

EXAMPLE D

*Prodenia litura*; breeding experiment on a treated nutrient medium

Glass Petri dishes 10 cm in diameter were treated with acetonic formulations of the active ingredients (a); after the solvent had evaporated, 5 caterpillars in the fourth larval stage were placed in the dishes, over which a cover was then placed. After 4 hours the kill rate was ascertained and 5 surviving caterpillars (10 to 12 mm long) were placed in 250 ml beakers. These beakers contained about 100 ml of a standard nutrient medium (3.1 liters of water, 80 g of agar, 137 g of brewers' yeast, 515 g of corn meal, 130 g of wheat germ and conventional additives and vitaliquid, and perforated transparent lids were placed on the beakers. The experiment was run until the moths in a control experiment (without active ingredient) emerged.

At an active ingredient concentration of 0.002 to 0.004 ppm, compounds 1 and 3 to 9 achieved 80 to 100% kill.

We claim:

1. A cyclopropanethiocarboxamide of the formula I $$R^2\text{-}\phi\text{-}O\text{-}\phi\text{-}O\text{-}CH(R^3)\text{-}(CH_2)_n\text{-}CH(R^4)\text{-}NH\text{-}CS\text{-}\triangleleft \quad (I)$$

where $R^1$ and $R^2$ are hydrogen, cyano, nitro, halogen, $C_1\text{-}C_4$alkyl or $C_1\text{-}C_4$alkoxy, the alkyl and alkoxy radicals being partially or completely halogenated; $R^3$ and $R^4$ are hydrogen or $C_1\text{-}C_4$alkyl; and n is 0 or 1.

2. A cyclopropanethiocarboxamide of the formula I as set forth in claim 1, where $R^3$ and $R^4$ are hydrogen and n is 0.

3. A pesticidal composition containing a pesticidally effective amount of at least one cyclopropanethiocarboxamide I as set forth in claim 1 and inert additives.

4. A pesticidal composition as set forth in claim 3, containing from 0.1 to 99wt% of a cyclopropanethiocarboxamide of the formula I.

5. A process for combating pests, wherein an effective amount of a cyclopropanethiocarboxamide of the formula I as set forth in claim 1 is allowed to act on pests on their habitat.

6. A cyclopropanethiocarboxamide as defined in claim 1, wherein $R^1$ is F and $R^2$, $R^3$ and $R^4$ are each hydrogen.

7. A cyclopropanethiocarboxamide as defined in claim 1, wherein $R^2$ is 4-F and $R^1$, $R^3$ and $R^4$ are each hydrogen.

8. A cyclopropanethiocarboxamide as defined in claim 1, wherein $R^1$ is F, n is 0 and $R^2$, $R^3$ and $R^4$ are each hydrogen.

9. A cyclopropanethiocarboxamide as defined in claim 1, wherein $R^2$ is 4-F, n is 0 and $R^1$, $R^3$ and $R^4$ are each hydrogen.

10. A process as defined in claim 5, wherein the cyclopropanethiocarboxamide is [N-[4-(3-fluorophenoxy)-phenoxy]-ethyl]-cyclopropanethiocarboxamide.

11. A process as defined in claim 5, wherein the cyclopropanethiocarboxamide is [N-[4-(3-fluorophenoxy)-phenoxy]-ethyl]-cyclopropanethiocarboxamide.

* * * * *

UNITED STATES PATENT AND TRADEMARK OFFICE
CERTIFICATE OF CORRECTION

PATENT NO. : 5,132,326

DATED : July 21, 1992

INVENTOR(S) : Uwe KARDORFF et al.

It is certified that error appears in the above-identified patent and that said Letters Patent is hereby corrected as shown below:

Claim 11, column 12, line 14: "[N-[4-(3-fluorophenox-" should read -- [N-[4-(4-fluorophenox- --

Claim 5, column 11, line 12: "on" should read -- or --

Signed and Sealed this

Seventeenth Day of August, 1993

Attest:

BRUCE LEHMAN

Attesting Officer

Commissioner of Patents and Trademarks